United States Patent [19]

Picart

[11] 4,421,927
[45] Dec. 20, 1983

[54] NEW CINNAMOYL-CINNAMIC ACID DERIVATIVE, AND ITS USE AS PHARMACEUTICAL

[75] Inventor: Francois Picart, Dijon, France

[73] Assignee: Societe de Recherches Industrielles (S.O.R.I.), Paris, France

[21] Appl. No.: 314,041

[22] Filed: Oct. 22, 1981

[30] Foreign Application Priority Data

Oct. 23, 1980 [FR] France .................. 80 22693

[51] Int. Cl.$^3$ .................. C07C 69/76
[52] U.S. Cl. .................. 424/248.55; 560/51; 560/53; 562/459; 562/463; 260/501.13; 546/238; 546/239; 544/171; 544/403; 548/335; 548/346; 548/373; 548/565; 564/169
[58] Field of Search .................. 562/463, 459; 560/51, 560/53; 546/238, 239; 544/171, 403; 548/335, 346, 373; 564/169; 424/306, 317

[56] References Cited

U.S. PATENT DOCUMENTS

| | | | |
|---|---|---|---|
| 3,255,241 | 6/1966 | Schultz | 560/51 |
| 4,124,724 | 11/1978 | Agoro | 424/317 |
| 4,163,859 | 10/1979 | Sprenger | 560/53 |

FOREIGN PATENT DOCUMENTS 2278332  7/1975  France .
2383157  3/1978  France .

OTHER PUBLICATIONS

The Journal of Organic Chemistry, vol. 34, No. 3, Mar. 1969, G. H. Cleland: "The Meerwein Reaction in Amino Acid" . . . pp. 744–747.

Primary Examiner—Paul J. Killos
Attorney, Agent, or Firm—Schwartz, Jeffery, Schwaab, Mack, Blumenthal & Koch

[57] ABSTRACT

The present invention relates to a new cinnamoyl-cinnamic acid derivative selected from the group constituted by:

(i) the m-cinnamoyl-cinnamic acid derivatives of formula

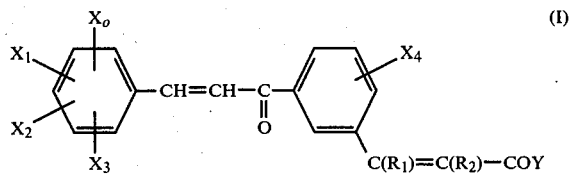

in which:
$X_o, X_1, X_2, X_3, X_4$, which are identical or different, each represent an atom of hydrogen, a halogen, a lower alkyl group, a lower alkoxy group, the group NRR' (where R and R' identical or different, each represent an atom of hydrogen or a lower alkyl group), the group $NO_2$, $CF_3$ or OH;

$R_1$ represents an atom of hydrogen or a lower alkyl group;

$R_2$ represents an atom of hydrogen or the methyl group;

Y represents a group OH, $OR_3$ (where $R_3$ is a lower alkyl group), NRR' (where R and R' are defined as hereinabove) or the group $O(CH_2)_n NR_4 R_5$ (where n is an integer of value 1 to 5—and preferably 2 or 3)—; and $R_4$ and $R_5$, identical or different, each represent an atom of hydrogen, a lower alkyl group and may form with the nitrogen atom to which they are bonded a heterocyclic group of 5 to 7 vertices capable of being substituted and of comprising one or more other heteroatoms such as N and O);

(ii) their geometrical isomers; and
(iii) their salts.

It also relates to its method of preparation and its use as pharmaceutical.

6 Claims, No Drawings

NEW CINNAMOYL-CINNAMIC ACID DERIVATIVE, AND ITS USE AS PHARMACEUTICAL

The present invention relates as a new industrial product to a chalcone which is a cinnamoyl-cinnamic acid derivative. It also relates to its method of preparation and to its use as pharmaceutical, particularly as growth regulator agent.

It has been surprizingly found that the compounds of formula I hereinafter, which are chalcones belonging to the family of cinnamoyl-cinnamic acid derivatives, are useful in therapeutics, particularly as growth regulator agents. They allow the restoration of a cellular phenotype of normal cell in a transformed cell (for example a cell with anarchic growth) and are useful in the treatment of diseases associated with an anarchic development of cells and in particular in the treatment of skin disorders such as psoriasis, cutaneous keratosis, acne, eczema.

The new cinnamoyl-cinnamic acid derivative according to the invention is characterized in that it is selected from the group constituted by:
(i) the m-cinnamoyl-cinnamic acid derivatives of formula:

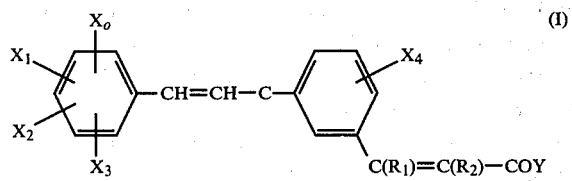

in which:
$X_0$, $X_1$, $X_2$, $X_3$, $X_4$, which are identical or different, each represent an atom of hydrogen, a halogen, a lower alkyl group a lower alkoxy group, the group NRR' (where R and R', identical or different, each represent an atom of hydrogen or a lower alkyl group), the group $NO_2$, $CF_3$ or OH;

$R_1$ represents an atom of hydrogen or a lower alkyl group;

$R_2$ represents an atom of hydrogen or the methyl group;

Y represents an OH group or $OR_3$ (where $R_3$ is a lower alkyl group), NRR' (where R and R' are defined as hereinabove) or the group $O(CH_2)_nNR_4R_5$ (where n is an integer having a value of 1 to 5- and preferably 2 or 3-; and $R_4$ and $R_5$, which are identical or different, each represent an atom of hydrogen, a lower alkyl group and may form with the nitrogen atom to which they are bonded a heterocyclic group of 5 to 7 vertices capable of being substituted and of comprising one or more other heteroatoms such as N and O);

(ii) their geometrical isomers; and
(iii) the salts of the compounds of formula I and of their geometrical isomers.

Lower alkyl group is understood here to mean a branched or straight hydrocarbon radical containing 1 to 4 atoms of carbon such as for example the methyl, ethyl, propyl, isopropyl, n-butyl, isobutyl or tertiobutyl groups. Similarly, lower alkoxy group is understood here to mean a group of which the hydrocarbon radical contains 1 to 4 carbon atoms.

Halogen is understood here to mean an atom of fluorine, an atom of chlorine, an atom of bromine or an atom of iodine, the preferred halogen atoms being the atom of fluorine and of chlorine.

Cycle with 5 to 7 vertices which may be substituted and may possibly contain one or more other heteroatoms may be constituted, in particular, by the pyrrolyl, imidazolyl, pyrazolyl, imidazolidinyl, pyrrolidinyl, pyrazolidinyl, piperidyl, piperazinyl, morpholinyl, homopiperidinyl, 4-methylpiperidyl, 4-methylpiperazinyl, 4-phenylpiperazinyl, 4-p-chlorophenyl-piperazinyl and 4-β-hydroxyethylpiperazinyl groups.

The geometrical isomers of the compounds according to the invention may be of "cis-cis", "trans-trans", "cis-trans" and "trans-cis" configuration. The modi operandi described hereinbelow lead to products which are essentially of "trans-trans" configuration, as demonstrated by NMR.

Salts are understood here to mean (i) the mineral salts obtained from an acid of formula I (Y=OH) with a mineral base (particularly NaOH, KOH, $NH_3$, Ca-$OH)_2$, (ii) the acid addition salts obtained from an acid of formula I (Y=OH) with an organic base and (iii) the acid addition salts obtained from a compound of formula I having at least one basic radical with a mineral or organic acid.

The preferred compounds are m-cinnamoyl-cinnamic acid derivatives such as Y=OH, alkoxy with 1 to 4 C atoms, β-(4-methylpiperazinyl)-ethyloxy; $X_0$=H, $CH_3$; $X_1$=H, Cl, $OCH_3$; $X_2$=H, $OCH_3$; $X_3$=H, $OCH_3$; $X_4$=H, $OCH_3$; $R_1$=H or $CH_3$ and $R_2$=H.

The method of preparation recommended according to the invention for preparing a compound of formula I is characterised in that an acetyl-cinnamic acid derivative of formula:

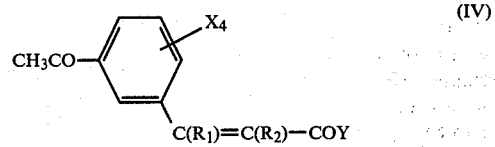

(where $X_4$, Y, $R_1$ and $R_2$ are defined as hereinabove) is condensed with a benzaldehyde of formula:

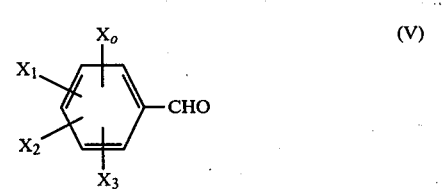

(where $X_0$, $X_1$, $X_2$ and $X_3$ are defined as hereinabove), and in that, the geometrical isomers are, if necessary, separated.

This reaction is advantageously made by reacting IV and V in an aqueous solution of an alkali (preferably an aqueous solution of NaOH at 400 g/l), or in a lower alcohol with 1 to 4 C atoms saturated by gaseous HCl. This technique is perfectly suitable for synthesis of acids I where Y is OH when operation is carried out in aqueous solution in the presence of an alkali such as sodium hydroxide, from an acid or an ester of formula IV. When operation is carried out in a lower alcohol saturated by gaseous HCl, the acid of formula IV yields the acid of formula I and, respectively, the ester of formula IV yields the ester of formula I; for obtaining an acid, the preferred lower alcohol is ethanol and for obtaining an ester, the preferred lower alcohol is the one corresponding to the ester group of compound IV.

The acid of formula I (Y=OH) may, if necessary, be subjected to a reaction of esterification or amidification to yield an ester or an amide. Similarly, the ester of formula I (Y=alkoxy with 1 to 4 C atoms) may, if necessary, be subjected to a reaction of saponification, transesterification or transamidification to yield an acid, an ester or an amide.

The separation of the geometrical isomers may be effected either after the condensation reaction or after the possible saponifications, esterifications and amidifications envisaged hereinabove. If this separation is considered necessary, it will preferably be carried out after the condensation reaction, the geometrical isomers thus obtained then, if necessary, being saponified, esterified or amidified.

The acetyl-cinnamic acid derivatives of formula IV [which are new intermediate products with the exception of the acids (Y=OH, $R_1=R_2=X_4=H$) and (Y=OCH$_3$, $X_4$=4-OH, and $R_1=R_2=H$) described in CA 84, 164 457q and respectively CA 89, 108 943m] may be prepared from a derivative of 2-methyl-2-phenyl-1,3-dioxolan of formula:

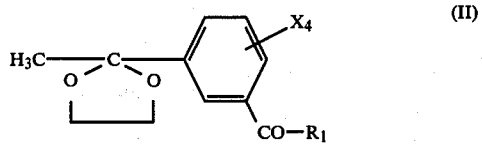

(where $X_4$ and $R_1$ are defined as hereinabove).

In a first step, a compound of formula II is condensed by means (a) either of a triethyl phosphonoalkanoate (and in particular triethyl phosphonoacetate or triethyl 2-phosphono-propionate) under the conditions of the reaction of HORNER-EMMONS, in the presence of sodium hydride in dimethylformamide;

(b) or of ethyl acetate in ethanol according to CLAISEN in the presence of sodium in xylene; to obtain the compound III of formula:

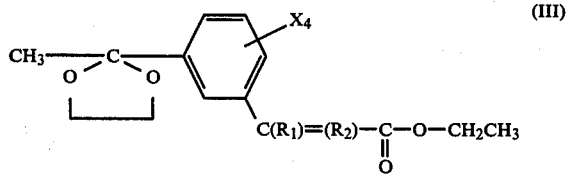

In a second step, the deprotection of the dioxolannyl group is effected by means of a concentrated acid (preferably 5 N HCl) then, to obtain the product IV used as raw material in the process of the invention, a saponification is for example carried out to have acid IV, then an esterification (or transesterification) to have the ester IV.

The invention also relates, as new intermediate products, to the compounds of formula IV where Y, $X_4$, $R_1$ and $R_2$ are defined as hereinabove with the additional condition that at least one of the $R_1$ and $R_2$ is different from H when $X_4$ is H or OH.

Non-limiting examples of preparation of cinnamoyl-cinnamic acid derivatives of formula I have been given hereinafter.

PREPARATION I

Obtaining of 3-[5-(p-chlorocinnamoyl)-2-methoxyphenyl]but-2-ene-oic acid (Example 9)

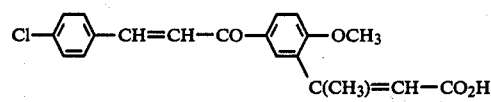

(a) Ethyl3-[5-(1,1-ethylenedioxy-ethyl)-2-methoxyphenyl]-but-2-ene-oate

At 0° C., 0.24 mole (54 g) of triethyl phosphonoacetate is added, drop by drop, to 0.3 mole (7.2 g) of sodium hydride in suspension in 500 ml of N,N-dimethylformamide. The reaction medium is allowed to return to ambient temperature (15°–25° C.) with stirring. After 5 hours, the emission of hydrogen has finished. The reaction medium is then taken to −40° C. and 0.2 mole (47 g) of 5-(1,1-ethylenedioxy-ethyl)-2-methoxyacetophenone is slowly added. It is allowed to return to ambient temperature and stirring is effected for 12 hours then hydrolysis on ice water. After extraction with ether, washing of the ethereal phases up to neutrality, drying and evaporation of the solvent, 45 g (yield=73%) of the expected product are collected, in the form of oil.

(b) 3-(5-acetyl-2-methoxy-phenyl)-but-2-ene-oic acid 45 g (0.147 mole) of the preceding ester are dissolved in 500 ml of ethanol and 200 ml of 10% sodium hydroxide. After heating the reaction medium for 2 hours at reflux, it is left to cool then acidified with 5 N hydrochloric acid. The expected product is allowed to precipitate and, after filtration, it is washed with water then alcohol. By recrystallisation in 150 ml of methanol, 15 g of the desired product are obtained m.p.=194° C.

(c) 3-[5-p-chlorocinnamoyl)-2-methoxyphenyl]-but-2-ene-oic acid 4.7 g (0.02 mole) of the acid previously obtained are dissolved in 30 ml of sodium hydroxide at 200 g/l. 2.8 g (0.02 mole) of para-chloro-benzaldehyde are added to the reaction medium and it is stirred for 2 hours. After acidification of the reaction mixture, the desired product precipitates. Filtering is effected, then the precipitate is washed in water. After recrystallisation in 300 ml of ethanol, 3 g of pure product are obtained. m.p.=215° C.

PREPARATION II

Obtaining of 3-(5-cinnamoyl-2-methoxyphenyl)-but-2-ene-oic acid (Example 5)

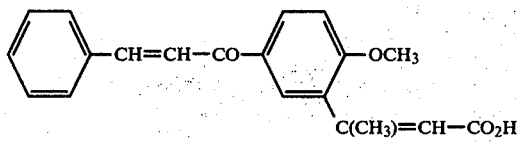

By proceeding as indicated in step (c) of preparation I, from 1 g (4.25 millimoles) of 3-(5-acetyl-2-methoxyphenyl)-but-2-ene-oic acid, 10 ml of sodium hydroxide at 200 g/l and 0.45 g (4.25 millimoles) of benzaldehyde, 1.1 g of the desired pure product is obtained. m.p. = 190° C.

PREPARATION III

Obtaining of 5-cinnamoyl-2-methoxy-cinnamic acid (Example 7)

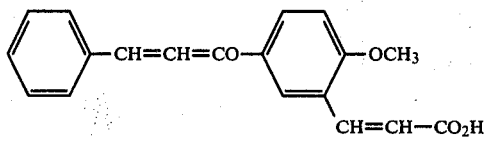

(a) ethyl 3-[5-(1,1-ethylenedioxyethyl)-2-methoxyphenyl]-prop-2-ene-oate

At 0° C., a mixture of 40 ml of ethyl acetate and 1 cm³ of ethanol is added drop by drop to a suspension of 3.5 g (0.15 mole) of sodium in balls in 200 ml of xylene. 22 g (0.1 mole) of 5-(1,1-ethylenedioxy-ethyl)-2-methoxy benzaldehyde dissolved in 50 ml of xylene are then added. The reaction medium is allowed to return to ambient temperature and is stirred for 3 hours. 50 ml of acetic acid are then added. After total disappearance of the sodium, 40 ml of water are added. After extraction with ether, washings with sodium hydroxide then with water up to neutrality, the ethereal phases are evaporated to obtain 24 g (oil) of the expected product.

(b) ethyl 3-(5-acetyl-2-methoxyphenyl)prop-2-ene oate 9.6 g of the ester obtained in step (a) are dissolved in 150 ml of ether and 20 ml of 5 N hydrochloric acid are added. Stirring is carried out for 12 hours. After extraction by the (1:1) v/v ether-CH$_2$Cl$_2$ mixture, then washings with water, 7.5 g of the expected product are obtained after evaporation of the organic phases. m.p. = 90° C.

(c) 3-(5-acetyl-2-methoxyphenyl)-prop-2-ene-oic acid 24 g (0.08 mole) of the ester obtained in step (b) are dissolved in 250 ml of methanol and 50 ml of sodium hydroxide at 400 g/l. After the reaction mixture is heated for 2 hours under reflux, it is left to cool then acidified with 5 N hydrochloric acid. The expected product is left to precipitate and, after filtration, is washed with water then with ethanol and finally with isopropyl ether. 13.6 g of the desired product are obtained. m.p. = 203° C.

(d) 3-(5-cinnamoyl-2-methoxyphenyl)-prop-2-ene oic acid

Using 10 g (0.045 mole) of the acid obtained in step (c), 80 ml of 20% sodium hydroxide and 5 g (0.045 mole) of benzaldehyde and according to a modus operandi similar to the one described in step (c) of preparation I, 11.5 g of the desired pure product are obtained, m.p. = 204° C.

PREPARATION IV

Obtaining of ethyl 3-[m-(p-chlorocinnamoyl]-prop-2-ene-oate (Example 3)

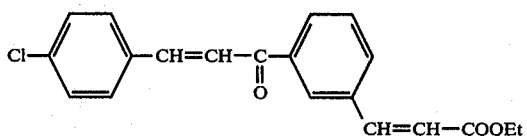

other nomenclature: ethyl m-(p-chlorocinnamoyl)-cinnamate 12 g (0.055 mole) of the ethyl ester of 3-acetyl-cinnamic acid are dissolved in 120 ml of ethanol. 8 g (0.057 mole) of para-chlorobenzaldehyde are added then 35 ml of anhydrous ethanol saturated with gaseous hydrochloric acid. The reaction medium is stirred for 10 hours.

By cooling the reaction medium to 0° C., the desired product precipitates. It is filtered then washed with hexane. 13.5 g (yield = 72%) of the expected pure product are thus obtained. m.p. 138° C.

A certain number of compounds according to the invention have been included in Table I hereinafter, in non-limiting manner.

The products according to the invention are used in therapeutics as agents promoting the restoration of a cellular phenotype of normal cell in a transformed strain. They may be used in particular for the topical or systemic treatment of skin disorders such as for example cutaneous keratoses, acne, psoriasis, eczemas, warts or any other skin disorder involving an alteration of the corneal tissue and for the treatment of inflammatory or degenerative alterations of the mucous membranes, cartilages, muscles or tendons, such as for example arthrosis, infectious rheumatism.

It will be recalled that, when normal cells (healthy cells) are cultivated on a given nutrient medium in a given space, it is observed that, after a certain lapse of time, the number of cells present is constant (confluence) and that, when transformed cells (abnormal cells of anarchic development) are cultivated under the same conditions, a constant number of cells is not obtained, as cellular proliferation does not cease (absence of confluence).

The pharmacological results obtained on a test for restoring the inhibition of growth with confluence of a culture of transformed cells are summarised hereinafter.

The modus operandi used is the one described by L. D. DION et al in J. Natl. Cancer inst. 58 (No. 3), pages 795-801 (1977) and summed up below. 20 000 murine cells are seeded on a surface of 0.2 cm² on a culture medium "Minimum Essential Medium" with Eagle salts and 10% of foetal calf serum. After 4 hours, the cells have adhered to the support. The culture medium is then replaced by the same medium containing the product to be tested dissolved in DM50.

At regular intervals over a period of two weeks, the cells are counted after trypsination. The growth curve obtained is compared with the one obtained in the absence of substance to be tested.

The effect of the drug is assessed by the minimum concentration necessary for inhibiting any growth from the moment when confluence is obtained.

The results obtained are given in Table II hereinafter which also shows the results relative to toxicity (LD-0 or LD-50) in the mouse by the intraperitoneal route.

An additional test was made with the product of Example 9, according to the test of inhibition of TPA-induced ornithine-decarboxylase activity (TPA being 12-O-tetradecanoylphorbol-13-acetate), described by A. K. VERMA et al in Cancer Research 38, 793–801 (1978).

The product in solution in 100 μl of acetone is tested by topical application on mice, an hour before topical application of 34 nmoles of TPA. The activity of the ornithine-decarboxylase is measured 4.5 hours after treatment with TPA. Under these conditions, an inhibition of 48% of the activity of the ornithine-decarboxylase is obtained by topical administration of 34 nmoles of the product of Example 9.

According to the invention, a therapeutical composition is recommended, characterised in that it contains, in association with a physiologically acceptable excipient, at least one compound of formula I, one of its geometrical isomers or one of their pharmaceutically acceptable salts.

The daily dosage which is recommended for the compounds according to the invention is from 0.1 to 50 mg per kg of body weight (preferably from 0.1 to 5 mg/kg) in the form of capsules or tablets, for oral administration.

TABLE I

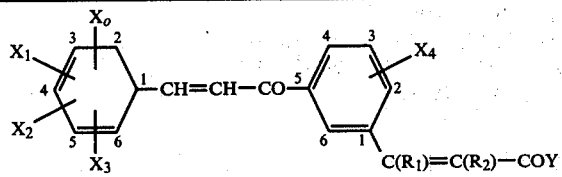

| Example | $X_o$ | $X_1$ | $X_2$ | $X_3$ | $X_4$ | $R_1$ | $R_2$ | Y | Melting point (0° C.) |
|---|---|---|---|---|---|---|---|---|---|
| 1 | H | 4-Cl | H | H | H | H | H | OH | 250 |
| 2 | H | 3-OCH$_3$ | 4-OCH$_3$ | 5-OCH$_3$ | H | H | H | OC$_2$H$_5$ | 133 |
| 3 | H | 4-Cl | H | H | H | H | H | OC$_2$H$_5$ | 138 |
| 4 | H | H | H | H | H | H | H | OH | 188 |
| 5 | H | H | H | H | 2-OCH$_3$ | CH$_3$ | H | OH | 190 |
| 6 | H | H | H | H | 2-OCH$_3$ | H | H | O(CH$_2$)$_2$—N(CH$_2$CH$_2$)$_2$N—CH$_3$ difumarate | 180 |
| 7 | H | H | H | H | 2-OCH$_3$ | H | H | OH | 209 |
| 8 | H | 4-OCH$_3$ | H | H | 2-OCH$_3$ | H | H | OH | 230 |
| 9 | H | 4Cl | H | H | 2-OCH$_3$ | CH$_3$ | H | OH | 215 |
| 10 | H | 4-Cl | H | H | 2-OCH$_3$ | H | H | OH | 242 |
| 11 | H | 4-Cl | H | H | 2-OCH$_3$ | CH$_3$ | H | NH$_2$ | 199 |
| 12 | H | 4-CH$_3$ | H | H | 2-OCH$_3$ | CH$_3$ | H | OH | 210 |
| 13 | H | 4-Cl | H | H | 2-OCH$_3$ | H | CH$_3$ | OH | 222 |
| 14 | H | 3-OCH$_3$ | 4-OCH$_3$ | 5-OCH$_3$ | 2-OCH$_3$ | CH$_3$ | H | OC$_2$H$_5$ | 120 |
| 15 | H | 2-CH$_3$ | H | H | 2-OCH$_3$ | CH$_3$ | H | OH | 202 |
| 16 | H | 2-Cl | H | H | 2-OCH$_3$ | CH$_3$ | H | OH | 232 |
| 17 | H | 3-Cl | 4-Cl | H | 2-OCH$_3$ | CH$_3$ | H | OH | 212 |
| 18 | 2-CH$_3$ | 3-CH$_3$ | 4-OCH$_3$ | 6-CH$_3$ | 2-OCH$_3$ | CH$_3$ | H | OH | 117 |
| 19 | H | 4-Cl | H | H | 2-OCH$_3$ | CH$_3$ | H | OC$_2$H$_5$ | 129 |
| 20 | H | 4-Cl | H | H | 2-OCH$_3$ | CH$_3$ | H | —O(CH$_2$)$_2$NEt$_2$ | 120 |
| 21 | H | 4-Cl | H | H | 2-OCH$_3$ | CH$_3$ | H | —N(CH$_2$CH$_2$)$_2$O | 140 |
| 22 | H | 4-Cl | H | H | H | CH$_3$ | H | OH | 189 |

The proof of the "trans-trans" configuration of the product of Example 18 has been brought by NMR study which gives:
- double bond C=C of the chalcone group $J_{H-H}$ = 16 Hz
- double bond C=C of the cinnamic group $J_{H-H}$ = 1.1 Hz

TABLE II

| Example | i.p. toxicity mice (mg/kg) | Concentration of inhibition of growth with confluence in μg/ml |
|---|---|---|
| 1 | DL-0 ≧ 1600 | 5 to 10 |
| 2 | DL-0 ≧ 1600 | 10 |
| 3 | DL-0 ≧ 1600 | — |
| 4 | DL-50 = 450 | >10 |
| 5 | DL-50 = 550 | 5 to 10 |
| 6 | DL-50 = 300 | — |
| 7 | DL-50 = 1000 | — |
| 8 | DL-0 ≧ 800 | >10 |

TABLE II-continued

| Example | i.p. toxicity mice (mg/kg) | Concentration of inhibition of growth with confluence in μg/ml |
|---|---|---|
| 9 | DL-0 ≧1600 | 5 |

± = Reference product: retinoic acid: 5 μg/ml

What is claimed is:

1. A new cinnamoyl-cinnamic acid derivative, characterised in that it is selected from the group consisting of:

(i) the m-cinnamoyl-cinnamic acid derivatives of formula:

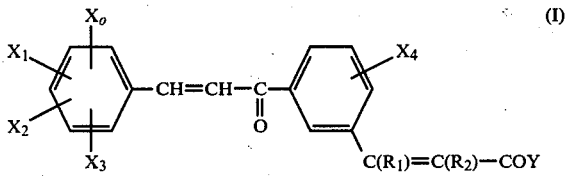

wherein:

$X_0$, $X_1$, $X_2$, $X_3$, $X_4$, are identical or different, and are selected from the group consisting of hydrogen, a halogen, a lower alkyl group, a lower alkoxy group, the group NRR' (where R and R', identical or different, are selected from the group consisting of hydrogen or a lower alkyl group), the group $NO_2$, $CF_3$ or OH;

$R_1$ represents hydrogen or a lower alkyl group;

$R_2$ represents hydrogen or the methyl group;

Y represents a group OH, $OR_3$ (where $R_3$ is a lower alkyl group), NRR' (where R and R' are defined as hereinabove) or the group $O(CH_2)_nNR_4R_5$ (where n is an integer of value 1 to 5- and preferably 2 or 3-; and $NR_4R_5$ is selected from the group consisting of the pyrrolyl, imidazolyl, pyrazolyl, imidazolidinyl, pyrrolidinyl, pyrazolidinyl, piperidyl, piperazinyl-morpholinyl, homopiperidinyl, 4-methylpiperidyl, 4-methyl-piperazinyl, 4-phenylpiperazinyl, 4-p-chlorophenylpiperazinyl and 4-β-hyroxyethyl-piperazinyl groups;)

(ii) their geometrical isomers; and (iii) their salts.

2. A new derivative according to claim 1, characterised in that Y is OH, alkoxy with 1 to 4 C atoms, $NH_2$, $O(CH_2)_2N(C_2H_5)_2$, morpholino or β-(4-methyl-piperazinyl)-ethoxy, $X_0$ is H or $CH_3$, $X_1$ is H, Cl or $OCH_3$, $X_2$ is H or $OCH_3$, $X_3$ is H or $OCH_3$, $X_4$ is H or $OCH_3$, $R_1$ is H or $CH_3$ and $R_2$ is H.

3. 3-{5-[(2,3,6-trimethyl-4-methoxy) cinnamoyl]-2-methoxyphenyl}-but-2-ene-oic acid.

4. 3-(5-cinnamoyl-2-methoxyphenyl)-but-2-ene-oic acid.

5. 3-[5-(p-chlorocinnamoyl)-2-methoxyphenyl]-but-2-ene-oic acid.

6. A therapeutical growth regulating composition, characterised in that it contains, in association with a physiologically acceptable excipient, an effective amount of at least one cinnamoyl-cinnamic acid derivative according to claim 1 as active ingredient.

* * * * *